United States Patent [19]

Mauchien et al.

[11] Patent Number: 4,641,032
[45] Date of Patent: Feb. 3, 1987

[54] PROCESS FOR THE DETERMINATION OF TRACES OF URANIUM IN SOLUTION BY TIME RESOLUTION SPECTROFLUORIMETRY

[75] Inventors: Patrick Mauchien, Orsay; Philippe Cauchetier, Massy, both of France

[73] Assignee: Commissariat a l'Energie Atomique, Paris, France

[21] Appl. No.: 712,175

[22] Filed: Mar. 15, 1985

[30] Foreign Application Priority Data

Mar. 16, 1984 [FR] France .................................. 84 04094

[51] Int. Cl.$^4$ .............................................. G01N 21/64
[52] U.S. Cl. .................................... 250/459.1; 356/318
[58] Field of Search ............... 250/459.1, 458.1, 461.1; 356/318

[56] References Cited

U.S. PATENT DOCUMENTS

| | | | |
|---|---|---|---|
| 4,198,568 | 4/1980 | Robbins et al. | 250/459.1 |
| 4,236,071 | 11/1980 | Chimenti | 250/253 |
| 4,239,964 | 12/1980 | Robbins et al. | 250/255 |
| 4,259,574 | 3/1981 | Carr et al. | 250/302 |
| 4,464,568 | 8/1984 | Brown et al. | 250/253 |

FOREIGN PATENT DOCUMENTS 1064726 10/1979 Canada .................................. 250/253

OTHER PUBLICATIONS

V. I. Balykin, V. S. Letokhov, V. I. Mishin and V. A. Semchishen "Laser Detection of Low Concentrations of Uranium Atoms Produced in a Chemical Reaction" *JETP Lett.* vol. 24, No. 8, (20 Oct. 1976) pp. 436–438.

R. M. Measures, W. R. Houston and D. G. Stephenson "Analyzing Fluorescence Decay" *Laser Focus* (Nov. 1974) pp. 49–52.

*Primary Examiner*—Janice A. Howell
*Assistant Examiner*—Constantine Hannaher
*Attorney, Agent, or Firm*—Kerkam, Stowell, Kondracki & Clarke

[57] ABSTRACT

Process for the determination of traces of uranium in solution by the spectrofluorimetry method. The fluorescence of the uranium molecules in the solution is excited by a pulsed laser shot. The exponential decay curve of this fluorescence is studied for a given wavelength. The value $F_O$ of said same fluorescence is deduced at the end of each laser pulse and is compared with the value $F'_O$ obtained for a standard uranium solution and containing a known uranium quantity.

2 Claims, 3 Drawing Figures

PROCESS FOR THE DETERMINATION OF TRACES OF URANIUM IN SOLUTION BY TIME RESOLUTION SPECTROFLUORIMETRY

BACKGROUND OF THE INVENTION

The present invention relates to the procedures used for determining traces of uranium present in an aqueous solution by spectrofluorimetry.

When it is wished to determine uranium in trace state in solutions, e.g. in radioactive effluents, it is known that spectrofluorimetry is the most suitable and most widely used method (cf e.g. the article entitled "Determination of uranium traces in a reprocessing plant", AIEA Nuclear Safeguards Technology 1982, Vol. 1, 260/25).

It is also known that when working in a pure solution, the detection limit of such a method is close to 10 $\mu gl^{-1}$ and that this limit is a consequence of the presence of spurious emission phenomena, which are superimposed within the solution on the fluorescent spectrum of the uranium. FIG. 1 illustrates, as a function of the time plotted on the abscissa, the decrease or decay of the fluorescence intensities plotted on the ordinate of the actual uranium and all the spurious compounds in the solution. This superimposing during a time $t_1$ (up to the total decay of the spurious emission) of the spurious fluorescence and the fluorescence of the uranium makes it difficult to interpret the results. In current cases, time $t_1$ is approximately 20 $\mu s$, whilst uranium decay requires approximately 400 $\mu s$.

However, for certain applications, such as e.g. the determination of uranium in surface water or solutions containing large quantities of inhibitor elements, it is necessary to use a more sensitive procedure making it possible to measure traces with levels of approximately 1 $\mu gl^{-1}$.

Canadian Pat. No. 1,064,726 entitled "Apparatus and method for uranium determination" discloses a method making it possible to achieve such performance levels through the use of a pulsed laser as the excitation source. The corresponding equipment, marketed by the Canadian Company SCINTREX Limited under the name "UA3", is based on the fact that it is possible to see in FIG. 1 that the fluorescence lifetime of the uranium is longer than that of the organic substances leading to the spurious disturbances referred to hereinbefore.

Thus, by carrying out the fluorescence measurement at the end of an adequately long time after each shot to ensure that the emission of organic substances has completely disappeared, it is then possible to hope that a signal specific to the uranium will be measured.

Under certain conditions, this procedure makes it possible to lower the detection limit to a content of around 0.05 $\mu gl^{-1}$ for said equipment, which is adequate for the determination of assay of surface water, which is e.g. generally carried out during prospecting at geological sites.

However, a known apparatus still suffers from disadvantages, which are sometimes highly prejudicial and which can essentially be grouped around three main points indicated below.

(1) The optical device provided in the apparatus does not have a dispersive system making it possible to obtain the spectrum giving the fluorescence intensity as a function of the emission wavelength. However, as this spectrum is perfectly characteristic of uranium, its recording is the only way of ensuring that the actual measured signal corresponds to uranium.

(2) The apparatus has a time measuring window positioned in a fixed manner at 30 microseconds after each laser shot. This operating procedure is based on the hypothesis according to which the signal received after 30 microseconds can only come from uranium, i.e. that time $t_1$ of FIG. 1 is always less than 30 microseconds, but this hypothesis is not always satisfied. Moreover, in certain cases, particularly when the uranium is mixed with fluorescence inhibitors, the signal due to the uranium decreases much faster and becomes virtually 0 at 30 seconds. In this case, it is indispensable to be able to move the window in order to optimize the signal.

(3) The Scintrex apparatus does not make it possible to measure the lifetime of the excited state of the uranium or, and this amounts to the same thing, to follow the decay of its fluorescence over a period of time. However, this constitutes vital information concerning the composition of the solution and it forms the basis for the present invention.

Thus, the determinations carried out with the Canadian apparatus according to the method of known additions and this consists of measuring the intensity of a given fluorescent line of the uranium, (a) for the solution to be determined, (b) for solutions derived from the preceding solution and in which known uranium quantities have been added on each occasion.

This known method suffers from the serious disadvantage of requiring the successive preparation of at least two or three solutions, preventing any fast measurement and of leading to the destruction of the initial solution to be determined.

SUMMARY OF THE INVENTION

The present invention relates to a process for the determination of uranium traces in solution by the known spectrofluorimetry method which, by making it possible to reach and measure the decay time or lifetime of the fluorescence of the uranium, makes it possible to overcome all the aforementioned prior art disadvantages whilst using remarkably simple means.

The present invention therefore specifically relates to a process for the determination of traces of uranium in solution by the known spectrofluorimetry method consisting of exciting the fluorescence of the uranium molecules in the solution by a pulsed laser shot, wherein the exponential decay curve of said fluorescence is studied for a given wavelength, the value $F_0$ of said same fluorescence is deduced at the end of each laser pulse and it is compared with the value $F'_0$ obtained for a standard uranium solution containing a known uranium quantity.

The originality of the present invention is based on the fact that it reveals that it is possible, by measuring the decay curve of the fluorescence intensity of uranium, to obtain the value $F_0$ of said fluorescence immediately at the end of each pulse of the laser shot.

Thus, the fluorescence, which is a function of the time $F(t)$ can be written at all instants in accordance with the equation (1):

$$F(t) = F_0 e^{-t/\tau} \tag{1}$$

in which $F_0$ is the value of said fluorescence at the end of each pulse of the laser shot. Moreover, the value $F_0$ of this initial fluorescence can be written according to equation (2);

$$F_0 = k\epsilon.I.t_{irr}.[UO_2^{2+}] \quad (2)$$

in which k is an equipment factor, $\epsilon$ is the molar extinction coefficient of the uranyl at the wavelength of the laser, I is the intensity of the laser line, $t_{irr}$ is the irradiation time of each pulse, usually approximately 5 nanoseconds and $[UO_2^{2+}]$ is the concentration of the uranyl molecules in the solution to be examined.

It can be seen that for given laser operating conditions, value $F_0$ is proportional to the uranium concentration which it is wished to measure. However, this quantity $F_o$ is not generally accessible due to the already envisaged spurious emission phenomena, which mask the fluorescence of the uranium by being superimposed thereon for a varyingly long time $t_1$ after each excitation pulse.

Conversely, on measuring F(t) for different values of the time t chosen beyond $t_1$, in such a way that the spurious fluorescence has disappeared, it is possible to plot the straight line shown in FIG. 2 and whose equation corresponds to the logarithm of equation (1), i.e.:

$$LF(t) = LF_o - t/\tau \quad (3)$$

By experimentally plotting several points, such as e.g. points A, B and C in FIG. 2, it is possible to plot a straight line, whose slope gives the value of $1/\tau$, and the ordinate at the origin, the value of the logarithm of $F_0$, which finally makes it possible to calculate the value $F_0$.

However, the Applicant has found in a remarkable manner that, under certain fixed experimental conditions (characteristics of the emitting laser and the geometrical shape of the measuring container), said value $F_0$ is a constant which is independent of the measuring medium. Thus, it is possible, by measuring the value $F_0$ obtained on a sample to be determined with the corresponding value $F'_0$ obtained on a standard solution sample produced in the laboratory and containing a known uranium quantity, to obtain the direct determination of a solution by external calibration, which consists of comparing the result obtained on the sample with that of a reference solution.

This result constitutes an important and remarkable innovation, because in all other known fluorimetric methods, e.g. a continuous excitation method (e.g. using an ultraviolet lamp) or a time resolution method carried out with a pulsed laser shot, the signal obtained is closely dependent on the medium and the measuring conditions. It was then necessary to use the dosed addition method requiring the preparation of at least three solutions for each sample, which was an important handicap in most industrial applications, where simple and rapidly repetetive operating procedures are obviously sought.

DETAILED DESCRIPTION OF THE DRAWING AND A PREFERRED EMBODIMENT

Figure 3:
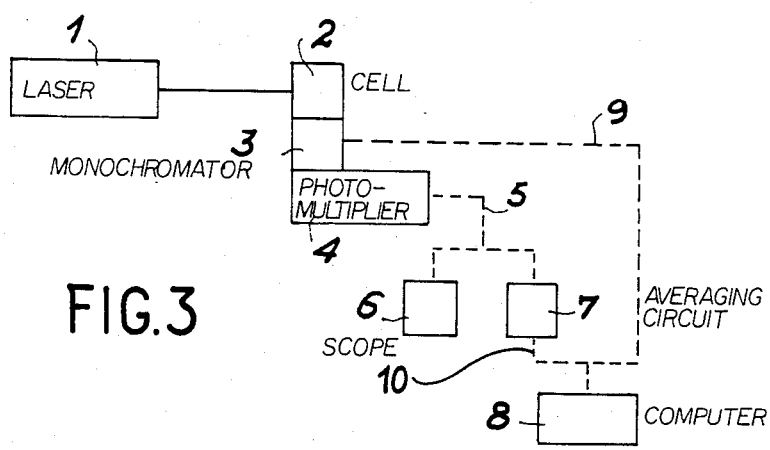
FIG. 3 is a diagrammatic view of an apparatus useful in performing the claimed process.

The invention will be better understood from the following description of a non-limitative embodiment with reference to FIG. 3, which very diagrammatically shows the apparatus used.

FIG. 3 diagrammatically shows a nitrogen laser 1 operating on a wavelength of 337 nanometers and which emits at a frequency of 30 Hz pulses lasting 5 nanoseconds. Obviously, these values are given for information purposes and could be increased or decreased without passing beyond the scope of the invention.

Figure 1:
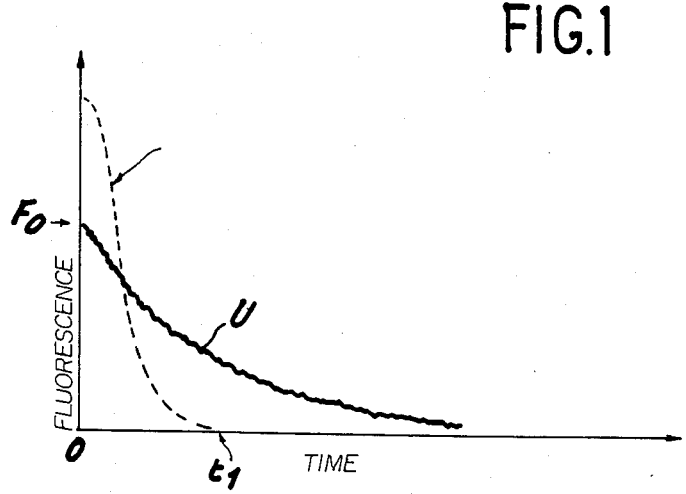
FIG. 1 illustrates the decay of trace uranium and spurious fluorescence intensities in solutions.
Figure 2:
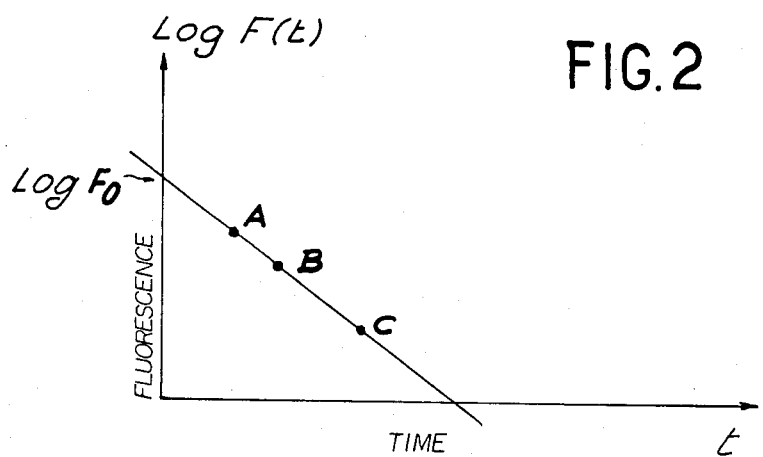
FIG. 2 is a graph useful in the deduction of $F_0$.

FIG. 3 also shows the measuring compartment or cell 2 containing the uranium molecules to be determined at valence 6 in the acid phosphate medium $PO_4H_3$. Behind measuring cell 2 is positioned a monochromator 3, which selects the wavelength chosen for examining the fluorescence. There is also a photomultiplier 4 which, on its output line 5, supplies electrical signals corresponding at all times to the intensity of the fluorescence emitted in the measuring compartment 2. These signals are distributed between an oscilloscope 6 making it possible to display the signals received and an averaging means 7 making it possible to both position the time reading window beyond $t_1$ in FIG. 1 and measure the intensity corresponding to said window position. Averaging means 7 is e.g. of type BOXCAR EGC model 162.

Finally, a Hewlett Packard model HP86 computer 8 makes it possible to acquire the data from averaging means 7, as well as to control, via line 9, monochromator 3 and via line 10, the positioning of the measuring window.

The present performance characteristics of the arrangement according to FIG. 3 are as follows.

It is possible to plot fluorescent spectra in a pure solution up to contents of approximately 0.02 $\mu gl^{-1}$. This is one of the best results obtained hitherto. The accuracy of the intensity measurement which can be carried out on these spectra depends on the considered content level the reproducibility of the measurements being approximately 10 to 15% for contents close to 1 $\mu gl^{-1}$.

With regards to the lifetime measurements, which constitutes an essential stage of the process according to the invention, the performances can be judged from two different standpoints.

The first standpoint relates to the sensitivity of the measurement. For relatively pure solutions in which the lifetime exceeds 100 microseconds, the apparatus of FIG. 3 makes it possible to carry out measurements up to contents close to 0.1 $\mu gl^{-1}$ with a reproducibility of approximately 10%. As far as is known to use, such a result cannot be achieved with any presently marketed equipment.

The second standpoint relates to the kinetic aspect of the response of the measuring chain. The arrangement shown in FIG. 3 makes it possible, for more concentrated solutions extending e.g. up to at least a few milligrams per liter, to measure the lifetime up to approximately 1 microsecond with a reproducibility of approximately 5%.

With regards to the fundamental measurement of the initial fluorescence $F_0$, the performances obtained are linked with the lifetime measurements. The detection limit in pure solution is approximately 0.1 $\mu gl^{-1}$. Such results make it possible to favourably envisage the determination by external calibration of most of the relevant solutions. At present, there is no equipment which is commercially available for carrying out such measurements, which is of major interest in all cases where the determination of uranium is used as an industrial process control means. The process according to the invention permits a simplification of particularly important operating procedures and consequently brings about considerable time savings. Finally, the use of the process according to the invention leads to interesting limitations in the volume of the effluents resulting from the analyses.

What is claimed is:

1. A process for the determination of traces of uranium in solution consisting of the steps of exciting the fluorescence of the uranium molecules in the solution by laser pulses, studying the exponential decay curve of said fluorescence for a given wavelength, deducing the value, $F_0$, of said same fluorescence at the end of each laser pulse and comparing the deduced value with the value, $F'_0$, obtained for a standard uranium solution containing a known uranium quantity.

2. A process for the determination of uranium traces according to claim 1, including setting the frequency of the laser pulses at approximately 30 Hz, setting the duration of each pulse at 5 nanoseconds and wherein the study of the exponential decay of the fluorescence of the uranium takes place at a wave length chosen by the operator in the fluorescent spectrum characteristic of uranium.

* * * * *